US 6,562,028 B2

(12) United States Patent
Nield et al.

(10) Patent No.: US 6,562,028 B2
(45) Date of Patent: May 13, 2003

(54) METHOD OF TREATING INTERVERTEBRAL DISCS BY INSERTING A DIFFUSER DIRECTLY INTO THE ANNULUS

(75) Inventors: Scott A. Nield, Reading, OH (US); Ronald J. Kolata, Cincinnati, OH (US); Martin J. Reynolds, Mansfield, MA (US); Paul G. Ritchie, Loveland, OH (US); Julianne M. Siegel, Cincinnati, OH (US)

(73) Assignee: Indigo Medical, Incorporated, Palo Alto, CA (US)

( * ) Notice: Subject to any disclaimer, the term of this patent is extended or adjusted under 35 U.S.C. 154(b) by 0 days.

(21) Appl. No.: 09/878,372

(22) Filed: Jun. 11, 2001

(65) Prior Publication Data

US 2001/0056278 A1 Dec. 27, 2001

Related U.S. Application Data

(60) Provisional application No. 60/210,756, filed on Jun. 12, 2000.

(51) Int. Cl.[7] .............................................. A61B 18/20
(52) U.S. Cl. ............................. 606/15; 606/13; 606/14; 606/16; 607/89
(58) Field of Search ................... 607/88–89; 606/12–18

(56) References Cited

U.S. PATENT DOCUMENTS

| | | | | | |
|---|---|---|---|---|---|
| 5,437,661 | A | * | 8/1995 | Rieser | 606/15 |
| 6,126,682 | A | * | 10/2000 | Sharkey et al. | 606/101 |
| 6,258,086 | B1 | * | 7/2001 | Ashley et al. | 604/510 |
| 6,270,492 | B1 | * | 8/2001 | Sinofsky | 606/101 |
| 6,290,715 | B1 | * | 9/2001 | Sharkey et al. | 604/510 |
| 6,361,530 | B1 | * | 3/2002 | Mersch | 606/27 |

* cited by examiner

Primary Examiner—Lee Cohen
Assistant Examiner—Henry M. Johnson, III

(57) ABSTRACT

A method of controllably heating the annulus of an intervertebral disc is disclosed. The method comprises the steps of forming an access channel through the annulus of an intervertebral disc while avoiding the nucleus of the intervertebral disc, inserting a light-emitting diffuser into the annulus, and activating the light-emitting diffuser to emit diffuse light while maintaining the light-emitting diffuser within the access channel to raise the temperature of the annulus to a value sufficient to cause a change in the characteristics of the annulus.

18 Claims, 10 Drawing Sheets

METHOD OF TREATING INTERVERTEBRAL DISCS BY INSERTING A DIFFUSER DIRECTLY INTO THE ANNULUS

This application claims the benefit of U.S. Provisional Application Ser. No. 60/210,756, filed Jun. 12, 2000.

This application is related to the copending U.S. patent application Ser. No. 09/878,238, filed Jun. 11, 2001, which is hereby incorporated by reference.

FIELD OF THE INVENTION

The present invention relates, in general, to a method of treating intervertebral discs to relieve back pain and, more particularly, a method of treating an intervertebral disc by using a light energy diffuser placed within the annulus of an intervertebral disc, while avoiding the nucleus of the intervertebral disc, and using the diffuser to heat a damaged portion of an annulus of the intervertebral disc by diffusing light energy directly into the annulus of the intervertebral disc.

BACKGROUND OF THE INVENTION

Degenerative disc disorders are difficult to treat. The normal pathway for treatment of lower back pain starts with a number of minimally invasive treatments including medications and exercise. Spinal surgery, such as spinal fusion or ablation of the nucleus, can also be used, but such surgeries are generally avoided because they are very invasive. A less invasive procedure is percutaneously applying heat to the annulus of the intervertebral disc.

Damage to the intervertebral disc in the spine is the main cause of lower back pain. The intervertebral disc, sometimes called a spinal disc or a disc, is a capsule with an annulus, comprising collagen, surrounding an inner volume called the nucleus. The nucleus contains a gel-like material. Damage to the annulus triggers the body to attempt to repair the injury. The repair attempt results in blood vessels and nerves growing into the damaged area of the annulus. It is believed that these new nerve endings are the source of "discogenic pain" and low back pain. Damage to the annulus also can result in weakening and bulging of the intervertebral disc. If the bulging puts pressure on nerve roots from the spinal cord the result is pain and nerve dysfunction.

It is well known that collagen responds to heat by shrinking and stiffening. In a damaged intervertebral disc where the damage has resulted in a bulge, heating the annulus to shrink the collagen in the annulus can help reduce the bulge. Heating the annulus to stiffen the collagen is also beneficial because the stiffer annulus reduces excessive movement of the spine. In addition, the heat applied to the annulus to shrink the collagen is beneficial because it damages or destroys nerve endings that may have grown into the damaged annulus thereby reducing the ability of the nerves to transmit pain. The combination of shrinking the collagen in the annulus and damaging or destroying the unwanted nerve endings is thought to be beneficial in reducing back pain.

Physicians have treated intervertebral disc pain utilizing radiofrequency current and lasers to damage nerve endings that have grown into the annulus. U.S. Pat. No. 5,433,739 to Sluijter et al describes a method of treating disc pain by utilizing radiofrequency current to heat the nucleus of an intervertebral disc. The nucleus is heated to a higher temperature than the annulus to transfer heat to the annulus of the intervertebral disc to raise the temperature of the intervertebral disc to a level that damages unwanted ingrown nerve endings. In U.S. Pat. No. 5,571,147, Sluijter et al describe a method of using laser light for heating the nucleus of an intervertebral disc.

Physicians have also treated disc pain utilizing lasers to ablate or vaporize the nucleus of an intervertebral disc. U.S. Pat. No. 5,958,008 to Daikuzono describes using a laser to vaporize the nucleus of an intervertebral disc.

Physicians have also treated disc pain by utilizing an electrically heated wire placed through the nucleus of an intervertebral disc to heat the annulus of the intervertebral disc to a temperature sufficient to cause the collagen in the annulus to shrink. The wire, which is heated by resistive heating, transfers heat by conduction to surrounding tissues. U.S. Pat. No. 6,122,549 to Sharkey et al describes a method to treat disc pain utilizing thermal resistive electric heating.

Ablating the nucleus or heating the annulus by inserting devices through the nucleus necessitates disturbing the tissues of the nucleus. It would be less invasive to avoid inserting devices into the nucleus by directly entering a damaged portion of the annulus from the outside of the annulus. Devices that heat by diffuse light energy use radiation to cause faster heat transfer and lower heating times than conduction. The faster heat transfer can be used to controllably heat a damaged zone of the annulus while maintaining adjacent tissues, such as the nucleus, at a temperature below that which would cause degradation. It would, therefore, be advantageous to develop a method of controllably heating an annulus of an intervertebral disc by diffusing light energy directly into the annulus, avoiding the nucleus, to avoid disturbing tissues such as the nucleus. It would further be advantageous to develop a method of controllably diffusing light energy directly into the intervertebral disc utilizing optical temperature feedback and control. It would further be advantageous to controllably and directly heat a portion of the annulus of an intervertebral disc utilizing light energy to avoid damaging a healthy portion of the spine.

SUMMARY OF THE INVENTION

The present invention is directed to a method of heating the annulus of an intervertebral disc by inserting a light diffuser directly into the annulus of an intervertebral disc from outside the disc while avoiding the nucleus. The present invention further includes a method of controllably shrinking collagen in the annulus of a intervertebral disc using a diffuse light source placed within the annulus to emit diffuse light energy directly into the annulus, optically measuring the temperature of the heated tissue, and adjusting light intensity based on the measured temperature. In particular, in a method according to the present invention, an optical fiber including a diffuser is placed into the annulus of an intervertebral disc percutaneously through a small diameter piercing needle or trocar. The fiber's diffuser is introduced from outside the annulus while avoiding the nucleus of the intervertebral disc. The fiber's diffuser is advanced to an area within the annulus needing heat to shrink collagen or to damage nerve endings. The light generator, such as a laser, is programmed to deliver light energy to raise the temperature of a region of the annulus tissue to a predetermined temperature for a predetermined length of time. The temperature can be, for example, a temperature sufficient to produce nerve damage of ingrown unwanted nerve endings in the annulus of an intervertebral disc or a temperature sufficient to produce shrinkage of collagen in the annulus of an intervertebral disc. In an optical fiber and light generator useful for an embodiment of the present invention, temperature monitoring of tissue near the optical fiber can be accomplished using fluorescent material placed within the optical fiber. The fluorescent material, when illuminated with a light in a wavelength emitted by the light generator, fluoresces with a light that decays in intensity with a time delay dependent upon the temperature of tissue near the material. Computerized control within the light generator monitors the returned fluorescent signal and controls power output and light intensity to control temperature of tissue near the optical fiber. A method according to the present invention further includes heating the annulus using an advantageous optical fiber that includes a continuous, unitary outer sleeve.

Detailed illustrative embodiments of laser fibers for implementing the present invention are disclosed. However, it should be recognized that various alternate structural elements may occur to those skilled in the art, some of which may be different from those specific structural and functional details that are disclosed.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
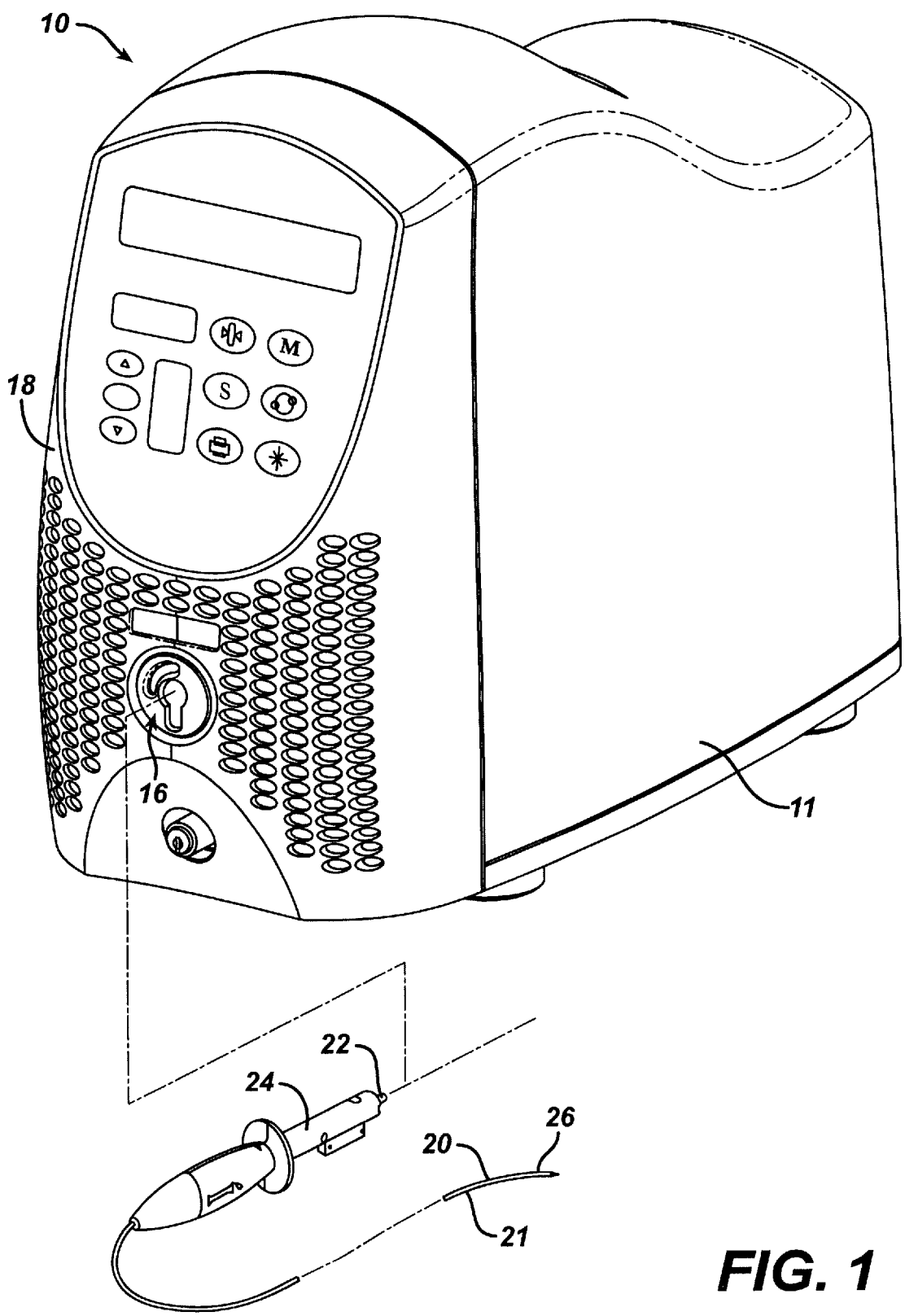
FIG. 1 is an isometric view of a laser treatment system, including a laser and an optical fiber, which may be used in a method according to the present invention.

FIG. 1 shows a laser treatment system 10 useful for heating of an annulus of an intervertebral disc by means of diffused light from an optical fiber 20. Laser treatment system 10 comprises laser 11 and optical fiber 20. A photodiode array is provided in laser 11 to produce a laser beam having a predetermined power and a predetermined wavelength useful for heating the intervertebral disc. For example, the predetermined power can be in a range of approximately 2–20 watts and the predetermined wavelength can be in a range of approximately 800–850 nanometers. As further seen in FIG. 1, an output port 16 is located within a front portion of housing 18 of laser 11. Output port 16 enables a laser beam to be optically linked with a first end 22 of optical fiber 20 via a connector 24 so that the laser beam can be transmitted to a second end 21 of optical fiber 20. Second end 21 of optical fiber 20 comprises an diffuser 26 emitting diffused laser light. A suitable laser 11 and corresponding optical fiber 20 is available from Ethicon-Endosurgery, Inc., in Cincinnati, Ohio, sold as the 830e LaserOptic™ Treatment system with optical fiber part number LF001. Another suitable laser 11, the Indigo® Optima laser, will be sold by Ethicon-Endosurgery, Inc., in Cincinnati, Ohio and is anticipated to be available in 2001. A suitable fiber for use with the Indigo® Optima laser will have a part number of LF002 and also expected to be available from Ethicon-Endosurgery, Inc., in Cincinnati, Ohio in 2001.

Figure 2:
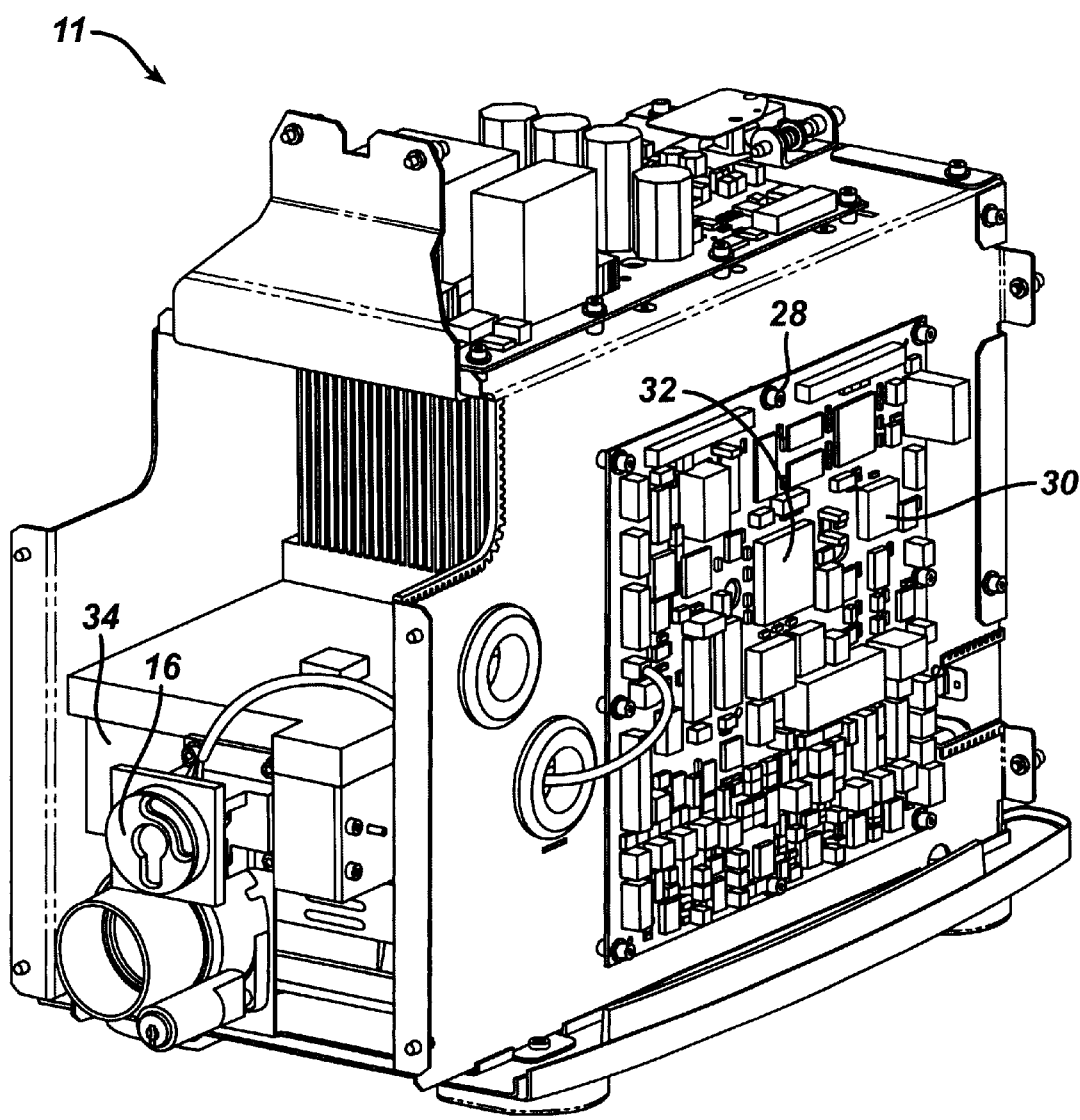
FIG. 2 is an isometric view of the laser illustrated in FIG. 1 with the housing removed to expose interior elements including the optical bench and controller board.

FIG. 2 depicts laser 11 with housing 18 removed to expose a controller board 28. It will be appreciated that, among other components, controller board 28 includes a main processor 30 that receives and processes electronic signals to control the operation of laser 11 and the intensity of the light radiated by diffuser 28. Diffuser 28 includes an optical temperature measurement device which may be, for example, a slug of silicone containing fluorescent material positioned at a distal end of fiber 20. The fluorescent material may be, for example, alexandrite. Signals from the optical temperature measurement device are detected by laser 11 and converted to electronic signals indicative of the measured temperature. Optical signals generated by the fluorescent material, when stimulated by light of an appropriate wavelength generated by laser 11, have a decay rate that is a function of temperature of the fluorescent material. The fluorescent material, embodied in a slug abutting the diffuser, has a temperature substantially equal to the temperature of the tissue adjacent the diffuser. If the laser stimulates the fluorescent material with light of an appropriate wavelength and an intensity that varies as a periodic function with respect to time, the fluorescent material will fluoresce with a light having a periodic function differing in phase from the phase of the stimulating signal. The light from the fluorescent material is then transmitted back to laser 11 by optical fiber 20. In laser 11 depicted in FIG. 2, a digital signal processor 32 is provided on controller board 28 to calculate the phase difference between the stimulating signal and the fluorescent light signal. The phase difference is a function of the temperature of the fluorescent material, and the phase difference can be used to measure the temperature of tissue adjacent the diffuser. Main processor 30 and digital signal processor 32 work in concert to assure that the necessary power is provided to laser 11 to maintain tissue near diffuser 26 at a desired temperature.

Laser 11 also includes an optical bench 34. Optical bench 34 directs the treatment laser beam, a marker laser beam, and the incoming fluorescence indicative of temperature. Optical bench 34 directs a laser beam through output port 16 and into optical communication with optical fiber 20 to provide heat to tissue. Optical bench 34, in addition to directing the laser beam which provides heat to tissue, directs a marker laser beam that illuminates the fluorescing material within optical fiber 20 to cause the fluorescing material to emit the temperature dependent returning light signal. Optical bench 34 also receives the light signals from the fluorescing materials within optical fiber 20 and utilizes light-sensing diodes to relay corresponding electrical signals to controller board 28 so that controller board 28 can use electrical components and software to calculate temperature.

Figure 3:
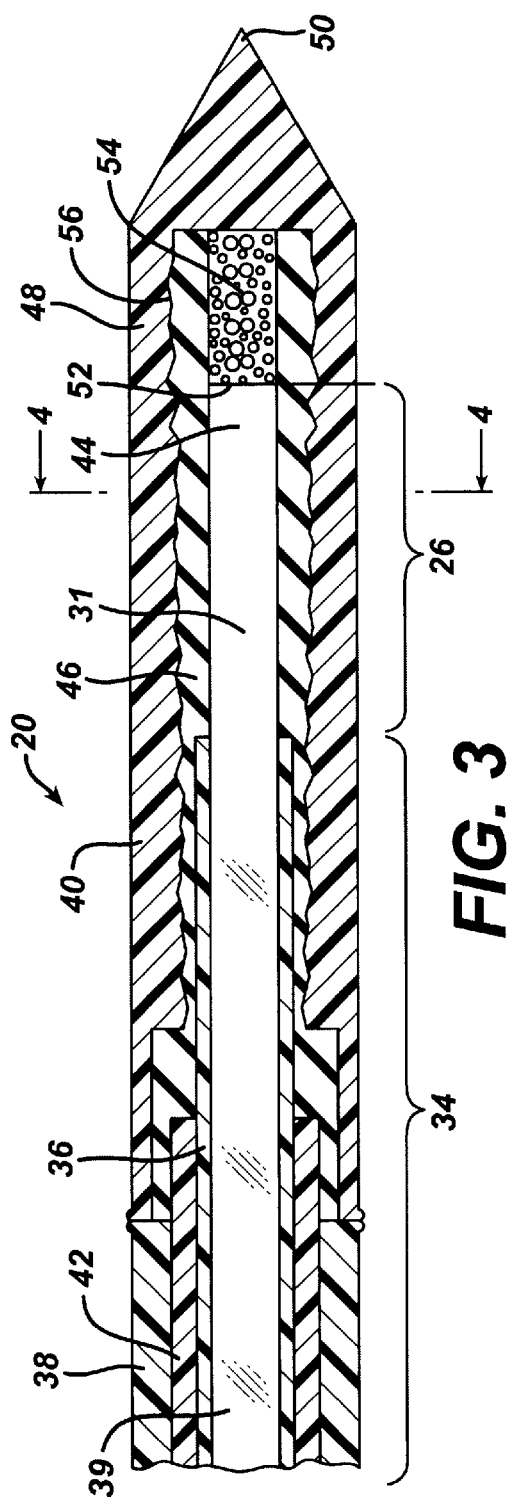
FIG. 3 is a cross-section view taken along the longitudinal axis of the distal end of one embodiment of an optical fiber illustrated in FIG. 1, including a diffuser.

FIG. 3 depicts a cross-section of a typical optical fiber 20 or light source that can be used for heating intervertebral discs. Optical fiber 20 includes diffuser 26 and a proximal light-transmitting portion 34. In light-transmitting portion 34 of optical fiber 20, cladding 36 and proximal portion 38 of outer sleeve 40 radially surround proximal portion 39 of core 31. Optical fiber 20 may also have a buffer layer 42 arranged to extend circumferentially between cladding 36 and proximal portion 38 of outer sleeve 40. The material used to form cladding 36 has an index of refraction lower than the index of refraction of the material used to create core 31 to contain light within core 31. Core 31, in addition to its proximal portion 39, extends through a distal portion 44 to distal face 52. Distal portion 44 of core 31 is surrounded by optical coupling layer 46 and distal portion 48 of outer sleeve 40. Outer sleeve 40 can consist of perfluoroalkoxy impregnated with barium sulfate.

A material having an index of refraction higher than the index of refraction of core 31 forms optical coupling layer 46, wherein UV50 Adhesive, available from Chemence, Incorporated, in Alpharetta, Ga., can be used to produce optical coupling layer 46.

A temperature measuring component 54 is filled with a temperature sensitive material and is fixed to distal face 52 of core 31. The temperature sensitive material can be, for example, alexandrite. Alexandrite fluoresces in a temperature dependent manner upon being stimulated by light, and this property is adapted to be used to measure temperature in tissue in proximity to diffuser 26. The same material can also reflect light back into the core to provide a more even or uniform light distribution. The same adhesive that is employed for optical coupling layer 46 can suspend the alexandrite particles to serve as the base material for temperature measuring component 54. Other chromium-doped garnets (e.g., yttrium, alexandrite, ruby and emerald), semiconductor doped glasses, phosphors, or other temperature dependent luminescent materials can be employed to measure temperature as these materials can also fluoresce in a temperature dependent manner.

As illustrated in FIG. 3, outer sleeve 40 is shaped to extend distally past temperature measuring component 54 and forms a pointed penetrating tip 50. A tip at the distal end of optical fiber 20 may take many forms if penetration is not needed, for example, rounded or blunt, as is suitable for the application. For example, a blunt tip may be used where diffuser 26 is introduced through a needle.

Figure 4:
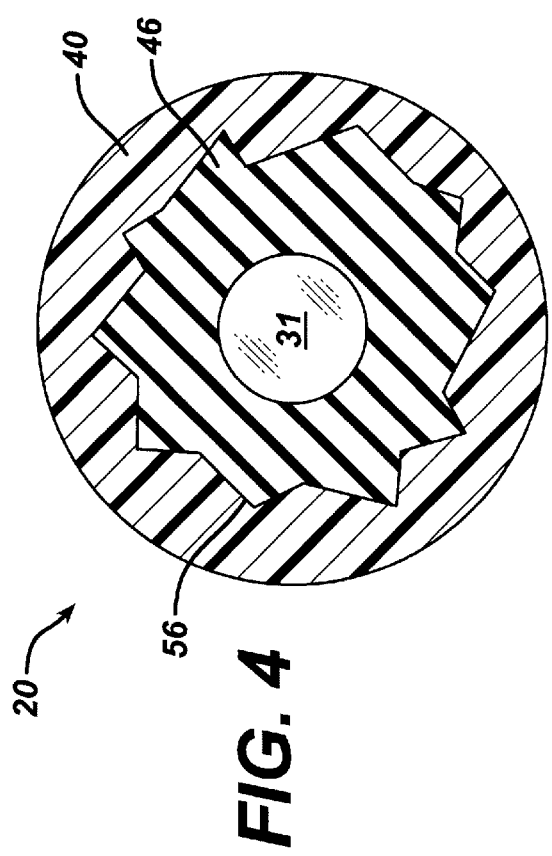
FIG. 4 is a cross-section view taken along 4—4 of FIG. 3 showing the interior of the diffuser portion of the optical fiber illustrated in FIG. 1 including abrasions on the inner circumference of the outer sleeve.

FIG. 4 depicts a section view of diffuser 26 showing abrasions 56 on the inner surface of distal portion 48 of outer sleeve 40. Abrasion of inner portion of outer sleeve 40 around the circumference and along the entire length of diffuser 26 results in substantially uniform light intensity distribution in a substantially cylindrical pattern. Abrasions can be applied by, for example, rubbing the inner surface of distal portion 48 of outer sleeve 40 with a brush or rough tool. It will be understood that other means of surface roughness can substitute for abrasion and can be created by other methods, such as, for example, molding a rough profile into the inner surface of outer sleeve 40.

Figure 5:
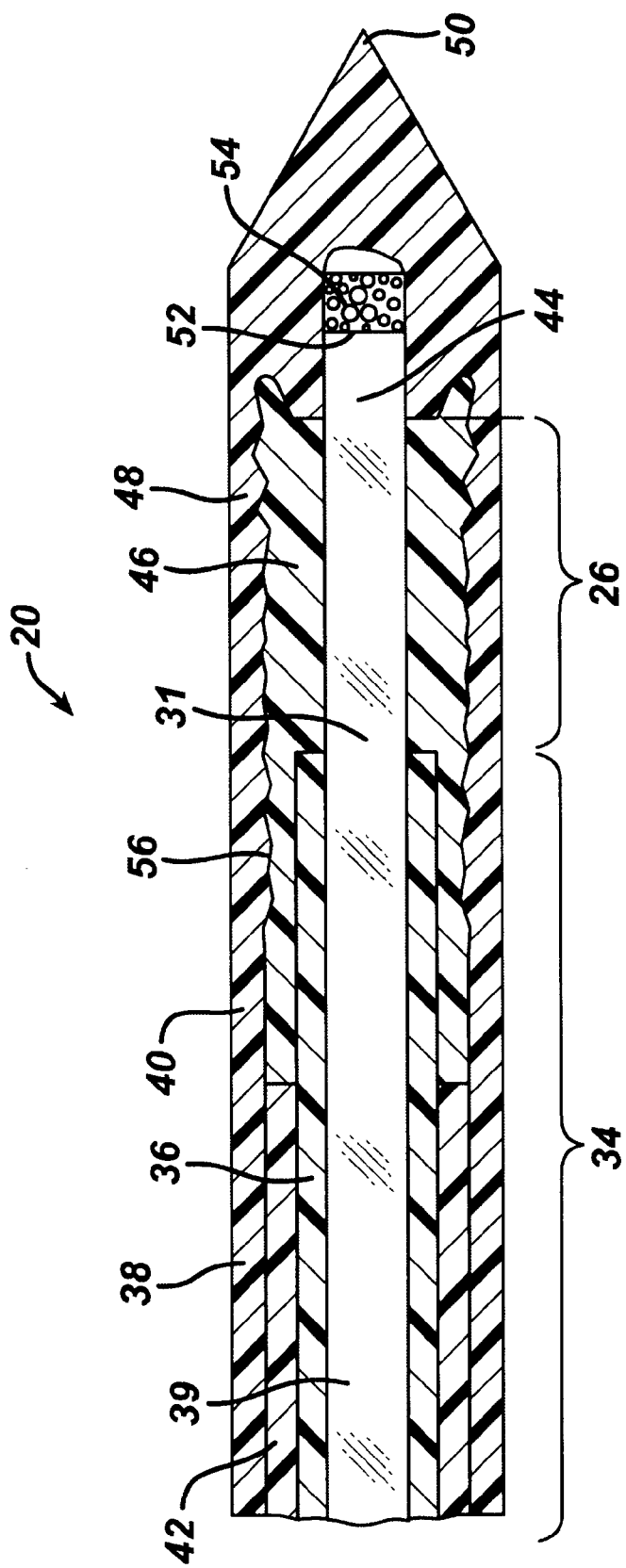
FIG. 5 is a cross-section view taken along the longitudinal axis of the distal end of an alternate embodiment of the optical fiber illustrated in FIG. 1 including a diffuser incorporating a continuous, unitary outer sleeve.

FIG. 5 depicts another embodiment of optical fiber 20 having a diffuser 26. The embodiment of diffuser 26 shown in FIG. 5 also comprises core 31 surrounded by optical coupling layer 46. Outer sleeve 40, further comprising abrasions 56 on its inner surface, is situated radially outwardly of optical coupling layer 46. Temperature measuring component 54 can be placed at distal end 52 of core 31. In the embodiment depicted in FIG. 5, there is no interruption, discontinuity, or weld joint on outer sleeve 40, so proximal portion 38 of outer sleeve 40 and distal portion 48 of outer sleeve 40 are two segments of one continuous unitarily constructed outer sleeve 40. Outer sleeve 40, as depicted in FIG. 5, has no weld joints or discontinuities in the outer diameter extending from the distal end of optical fiber 20 to connector 24 which conceivably tend to weaken optical fiber 20, or which may detrimentally catch or drag optical fiber 20 to displace it while in use. When using optical fiber 20, it may need to be bent to successfully locate the fiber in the body of a patient. Optical fiber 20 and the associated outer sleeve 40 are designed to withstand more bending than optical fibers with outer sleeves which have weld lines or discontinuities formed in the outer diameter proximal to penetrating tip 50. As in optical fiber 20 illustrated in FIG. 3, the tip at the end may take many forms, including a blunt tip.

U.S. patent application Ser. No. 09/785,571, filed Feb. 16, 2001, and hearby incorporated herein by reference, describes an embodiment of optical fiber 20 utilizing a continuous, unitary outer sleeve.

Referencing FIG. 5, when light is sent through optical fiber 20, light travels through core 31 to diffuser 26. In diffuser 26, light energy emerges from core 31 to optical coupling layer 46 because of the higher index of refraction of optical coupling layer 46. Distal portion 48 of outer sleeve 40 surrounds optical coupling layer 46 and collects the light from optical layer 46. To collect the light from optical layer 46, distal portion 48 of outer sleeve 40 employs abrasions 56 formed on the inner surface of distal portion 48 of outer sleeve 40. Outer sleeve 40 can use barium sulfate particles scattered within outer sleeve 40 to direct light energy evenly outwards towards the tissue. Diffuse light then emerges in all radial directions from outer sleeve 40 in the area of diffuser 26. Light energy reaching temperature measuring component 54 is reflected back towards core 31 by particles in temperature measuring component 54. Fluorescent properties of alexandrite particles, when stimulated by light energy of the proper wavelength, can determine the temperature of surrounding tissues by in a wavelength of light to be returned to laser 11. The fluorescence occurs with a temperature dependent time delay that laser 11 can sense using computer circuitry.

Figure 6:
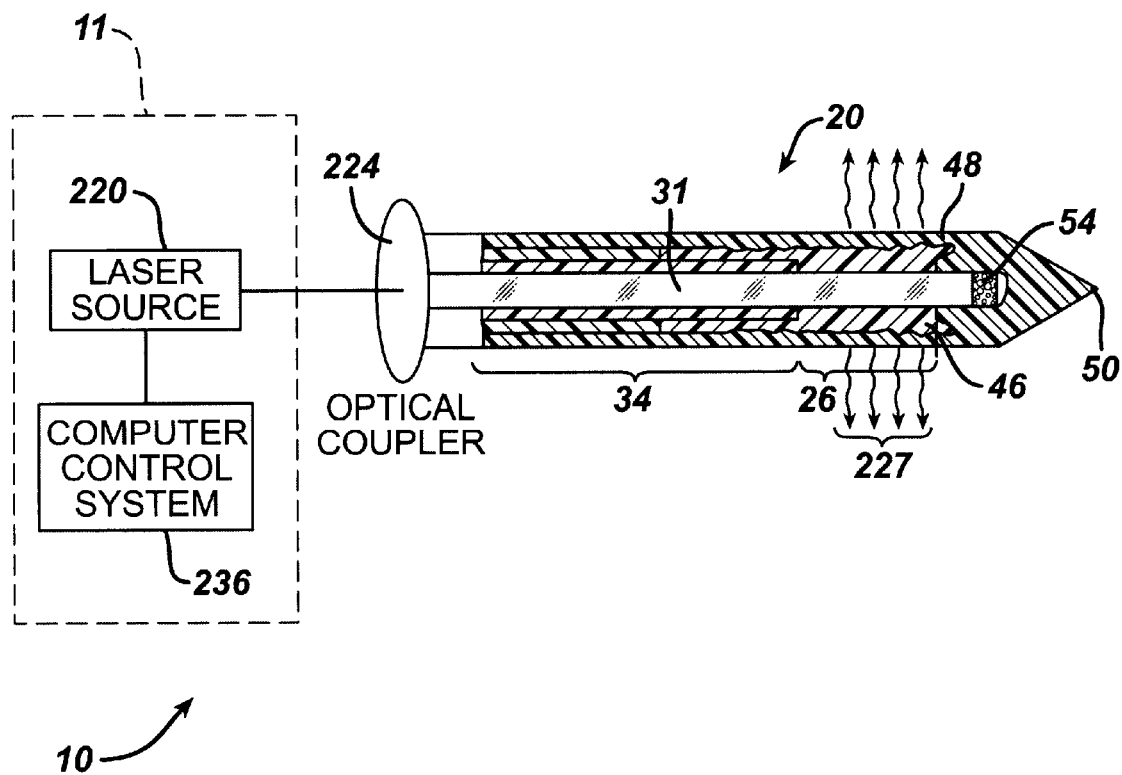
FIG. 6 is a block diagram of a laser treatment system, including one embodiment of a diffuser, which may be used in a method according to the present invention.

FIG. 6 depicts a block diagram of a of the operation of laser treatment system 10 utilizing optical fiber 20 incorporating the embodiment of diffuser 26 in FIG. 5. Laser source 220 working together with computer control system 236 for a laser 11 is useful for an embodiment of the inventive method. Laser source 220 and computer control system 236 may be housed together inside laser 11. Control system 236 may comprise any computer system for monitoring response from temperature measuring component 54, including main processor 30 and digital signal processor 32 arrayed on controller board 28. Control system 236 may control the light intensity of diffuser 26 using the monitored temperature. Optical coupler 224 can be, for example, output port 16.

Figure 7:
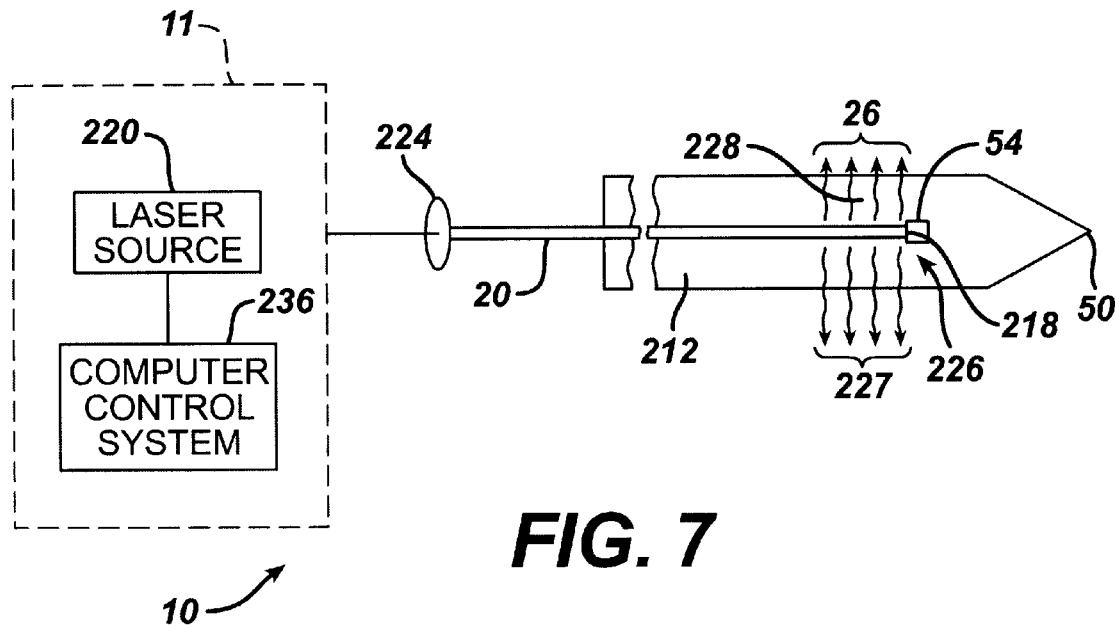
FIG. 7 is a block diagram of a laser treatment system, including an alternate embodiment of a diffuser, which may be used in a method according to the present invention.
Figure 8:
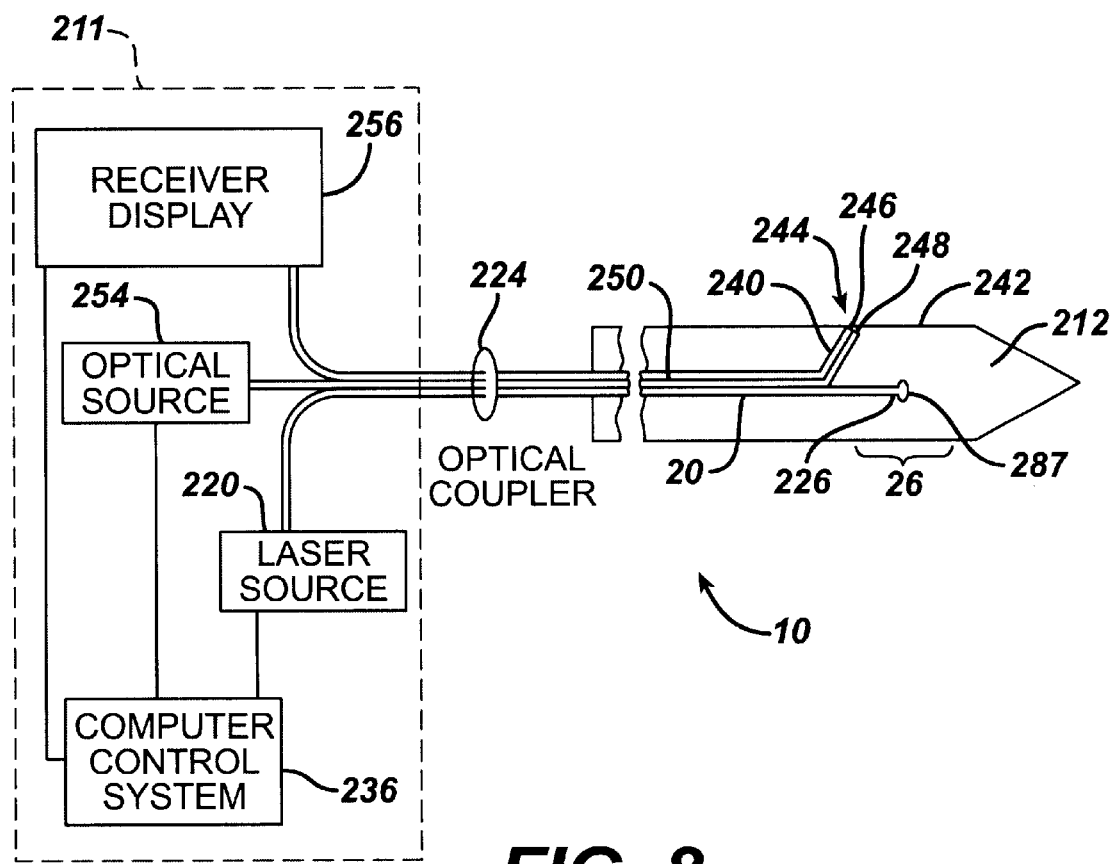
FIG. 8 is a block diagram of an alternate embodiment of a laser treatment system, which may be used in a method according to the present invention.

FIGS. 7 and 8 schematically show these other forms of diffusers used with laser treatment systems. A solid, generally cylindrical shaft 212 can be placed on the end of optical fiber 20. The optical fiber 20 is embedded in the material of the shaft axially central to the shaft. A cylindrical diffusing tip 218 is placed on the energy transmitting end of optical fiber 20. As illustrated in FIG. 7 by arrows 227, energy radiates outwardly from diffusing tip 218 and is transmitted through the shaft including a portion of the shaft located behind penetrating tip 50. Thus, diffusing tip 218, together with the portion of shaft 212 surrounding diffusing tip 218 become effectively a diffuser 26. Shaft 212 is constructed of optical quality plastic, such as polycarbonate, polysulfone, or polymethylmethacrylate (PMMA), so that laser energy may be transmitted through the entire diameter of the shaft.

In one embodiment of optical fiber 20 utilizing shaft 212, the outside diameter defined by shaft 212 may be as large as 3 mm. However, the size of the outside diameter will be determined by the desired usage. For example, when used for interstitial laser induced hyperthermia to treat BPH, a diameter range of about 0.8 to about 1.6 millimeters is appropriate. When used intraluminally in the urethra or the intervertebral disc, a diameter range of about 1 to about 4 millimeters is appropriate.

In the embodiment of FIG. 7, optical fiber 20 is connected to a laser source 220 through an optical coupler 224 so as to transmit light energy from the source to distal end 226 of the fiber that is connected to diffusing tip 218. Optical coupler 224 may take the form of output port 16 seen in FIG. 1. Laser source 220 may be within laser 11 shown in FIG. 1. In the embodiment of FIG. 7, optical fiber 20 is completely embedded in the material of shaft 212. The portion of shaft 212 containing the distal length of optical fiber 20 to penetrating tip 50 is referred to as the penetrating portion 228, i.e., a portion that is intended to penetrate into the tissue to be subject to treatment. As illustrated in FIG. 7, penetrating tip 50 of shaft 212 may be tapered or conically shaped.

Temperature measuring component 54 may be placed at distal end of optical fiber 20 similarly to the embodiment shown in FIG. 5. Temperature measuring component 54 may contain alexandrite or other fluorescing material to return light to measure temperature to computer control system 236. Computer control system 236 may be any computer system for monitoring response from temperature measuring component 54, including main processor 30 and digital signal processor 32 arrayed on controller board 28 and working to assure controlled light intensity from optical fiber 20. Computer control system 236 may reside within one physical housing 18 with laser source 220 to form laser 11.

Construction of the shaft 212 with its embedded optical fiber 20 and diffusing tip 218 can be by any convenient means. For example, optical fiber 20 with its diffusing tip 218 can be used as an insert in an injection mold and shaft 212 can be molded around the optical fiber so that otherwise exposed surfaces along the length of the optical fiber are in close contact with the shaft material. Alternatively, optical fiber 20, its diffusing tip 218, and the encapsulating shaft material can be co-extruded.

In tissues having moderate scattering, such as the core of the intervertebral disc, diffusing tip 218 must deliver energy to the outside surface of shaft 212 with both an acceptable energy density and a correct angle of incidence. Such diffusing tips are usually formed of quartz and are commercially available, such as the spherical and cylindrical diffusers from PDT Systems. The incorporation of a diffusing tip 218 onto the distal end of optical fiber 20, embedded within the interior of shaft 212, results in an increase of the diffusion of the laser energy prior to its contact with the tissue. The increased area of the surface utilized for diffusing light, (for example as compared to penetrating tip 50 if the end of optical fiber 20 were placed there) greatly lowers the irradiance of the power density at the tissue interface. This alleviates a problem of overheating at the tissue/shaft interface present when a bare tip is used, while irradiating the same volume of tissue.

Referring to FIG. 8, an optical fiber incorporating a diffuser 26 is shown in which optical temperature feedback and thermometry is accomplished through the use of a fiberoptic probe 240. A solid shaft 212 again embeds the distal length of an optical fiber 20, in this embodiment having a spherical dispersing tip 287. Optical fiber 20 can be connected to laser source 220 and computer control system 236. In the embodiment of FIG. 8, fiberoptic probe 240 is embedded side by side with temperature monitoring system optical fiber 250. Prior to distal end 226 of optical fiber 20, fiber optic probe 240 diverges upwardly to terminate at surface 242 of shaft 212. There, semiconductor sensor 244 is disposed to sense the temperature of the tissue. Such a sensor 244 can be fabricated of a suitable semiconductor material such as gallium arsenide in prismatic form having reflective faces 246 and 248. Semiconductor sensor 244 is optically coupled at the hypotenuse of the prism to the ends of fiber optic probe 240 and temperature monitoring system optical fiber 250. An optical source 254, emitting light for the temperature monitoring system, is connected to temperature monitoring optical fiber 250 while a receiver display 256 is connected to fiber optic probe 240. Monochromatic light emitted by optical source 254 strikes on of faces 248 of the prismatic configuration of the semiconductor or sensor 244 and is reflected to the other face 246 where it is reflected a second time as a transmitted ray along fiberoptic probe 240 connected to receiver display 256. As it transverses semiconductor sensor 244, the radiant energy is absorbed as a function of the temperature of sensor 244. Accordingly, the intensity of the transmitted light ray will be diminished as the temperature of semiconductor sensor 244 is increased. The intensity of the transmitted ray is readable as a temperature on receiver display 256. See Christenson U.S. Pat. No. 4,136,566 for a description of such semiconductor sensors.

It will be understood that optical temperature measurement as described in FIG. 8 could be communicated to a computer to control the light intensity of diffuser 26. Optical source 254 and receiver display 256 can reside with computer control system 236 and laser source 220 within an alternate embodiment of laser 211. Optical coupler 224 can couple optical fiber 20, fiber optic probe 240, and temperature monitoring optical fiber 250 to the alternate embodiment of laser 211.

Laser source 220 can emit light to optical fiber 20. Spherical dispersing tip 287, at the end of optical fiber 20 in the embodiment of FIG. 8, scatters light emitted from optical fiber 20, thus forming an embodiment of diffuser 26. The scattered light warms adjacent tissue. Optical source 254 emits light in the wavelength utilized for temperature monitoring and control. Returned light can be monitored through receiver display 256 attached to fiberoptic probe 240. Electrical signals within receiver display 256, representative of monitored light, can be forwarded to computer control system 236 for processing to control light intensity based on a temperature calculated by computer control system 236 from returned light.

A wide variety of scatters and dispersers can be accommodated by the solid shaft configuration. FIGS. 9 through 12 illustrate various structures without reference to thermometry.

Figure 9:
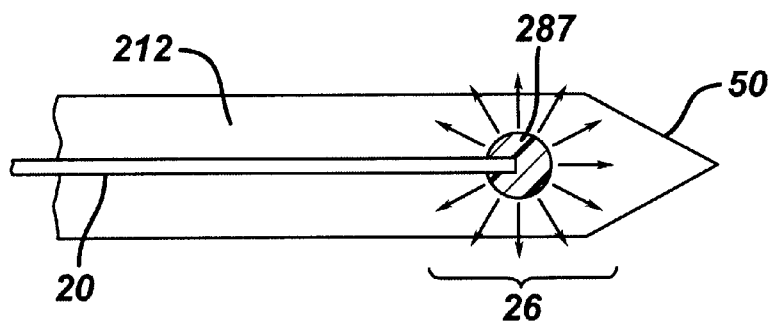
FIG. 9 is cross-section view of an embodiment of a diffuser, which may be used in a method according to the present invention, employing a spherical dispersing tip at the end of an optical fiber.

More specifically, referring to FIG. 9, an optical fiber 20 with a diffuser 26 is shown in which the distal end of optical fiber 20 and its spherical dispersing tip 287 is disposed adjacent to penetrating tip 50 of shaft 212. However, in this case, the assembly of optical fiber 20 and dispersing tip 287 is totally embedded in the material of the shaft 212. In FIG. 9, spherical dispersing tip 287 disperses light through a portion of shaft 212.

Figure 10:
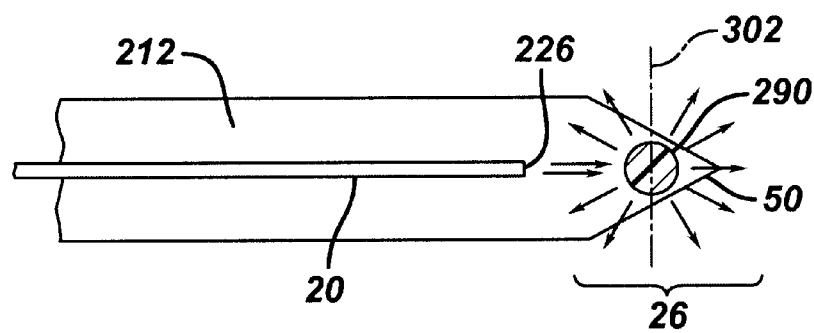
FIG. 10 is a cross-section view of an embodiment of a diffuser, which may be used in a method according to the present invention, incorporating a scatterer adjacent the penetrating tip.

In FIG. 10, rather than having a dispersing tip on the distal end 226 of optical fiber 20, a scatterer 290 is embedded adjacent penetrating tip 50 of shaft 212 which is constituted by the shaft material. Scatterer 290 may take any of many forms, such as a spherical ball, as shown, formed by plastic and loaded with refractive scattering power such as alumina, or may take other forms suitable for diffusing energy. The exact location of scatterer 290 is not critical. It acts to diffuse the energy transmitted from the energy transmitting end 226 of optical fiber 20 and to prevent the overheating of penetrating tip 50. The particular scatterer in the form shown in FIG. 10 can be obtained by mixing 30% of alumina in epoxy and forming the material into balls of suitable size, e.g., about 1.5 millimeters in diameter. Scatterer 290 scatters light rays through shaft 212 in the vicinity of scatterer 290 to cause the shaft 212 in the vicinity of scatterer 212 to become diffuser 26.

In the manufacture of devices such as illustrated in FIG. 10, one can injection mold the shaft 212 around optical fiber 20, terminating at a dividing line, indicated generally at 302 in FIG. 10. In each case, a second piece of shaft is manufactured that mates with the first piece having an interior shape to accommodate scatterer 290. PMMA is amorphous, in the nature of glass, having a glass transition temperature allowing it to be worked in the manner of glass so that upon heating and annealing, a uniform integral body is obtained.

Figure 11:
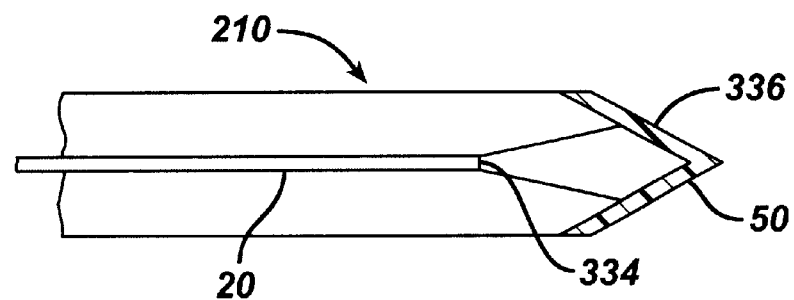
FIG. 11 is a cross-section view of an embodiment of a diffuser, which may be used in a method according to the present invention, utilizing the penetrating tip to determine the spread of the laser beam.

FIG. 11 illustrates the incorporation of a flat ended optical fiber 20 which is spaced a distance between distal transmitting end 334 of optical fiber 20 and penetrating tip 50 to determine the spread of the laser beam. By placing the energy transmitting end 334 of optical fiber 20 set back from penetrating tip 50, the angular spread of the energy transmitted is increased. Refractive scattering material 336, such as diamond powder, is disposed with the surface of penetrating tip 50 and serves to diffuse the energy transmitted from optical fiber 20. Scattering material 336 may be placed in a separately molded conical component, joined to the main shaft as discussed with respect to FIG. 9, or may be coated on the outer surface of penetrating tip 50.

Figure 12:
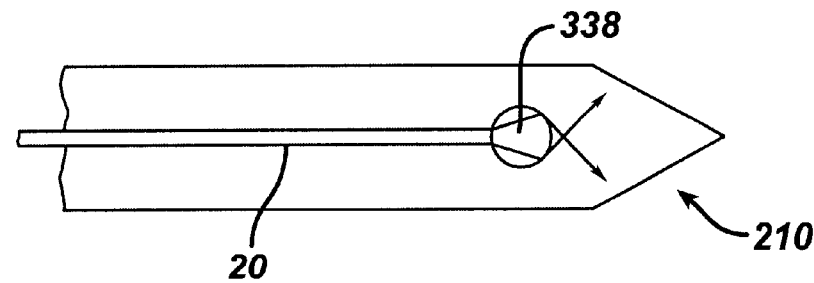
FIG. 12 is a cross-section view of an embodiment of a diffuser, which may be used in a method according to the present invention, incorporating a lens.

Referring to FIG. 12, the incorporation of a lens 338 positioned at the energy transmitting end of optical fiber 20 is illustrated. Divergence of energy transmitted from optical fiber 20 may be induced by bringing the energy to a focus with lens 338. In the embodiment illustrated, a spherical lens 338 is mounted on the end of the optical fiber 20, for example, with appropriate clear adhesive and the entire assembly is injection molded with material constituting shaft 212. The lens 338 may be a spherical lens, a high-refractive indexed negative lens, e.g., of sapphire, or any other suitable lens capable of diverging the energy of the laser light. Lens 338 diffuses light towards the outer surface of shaft 212.

Figure 13:
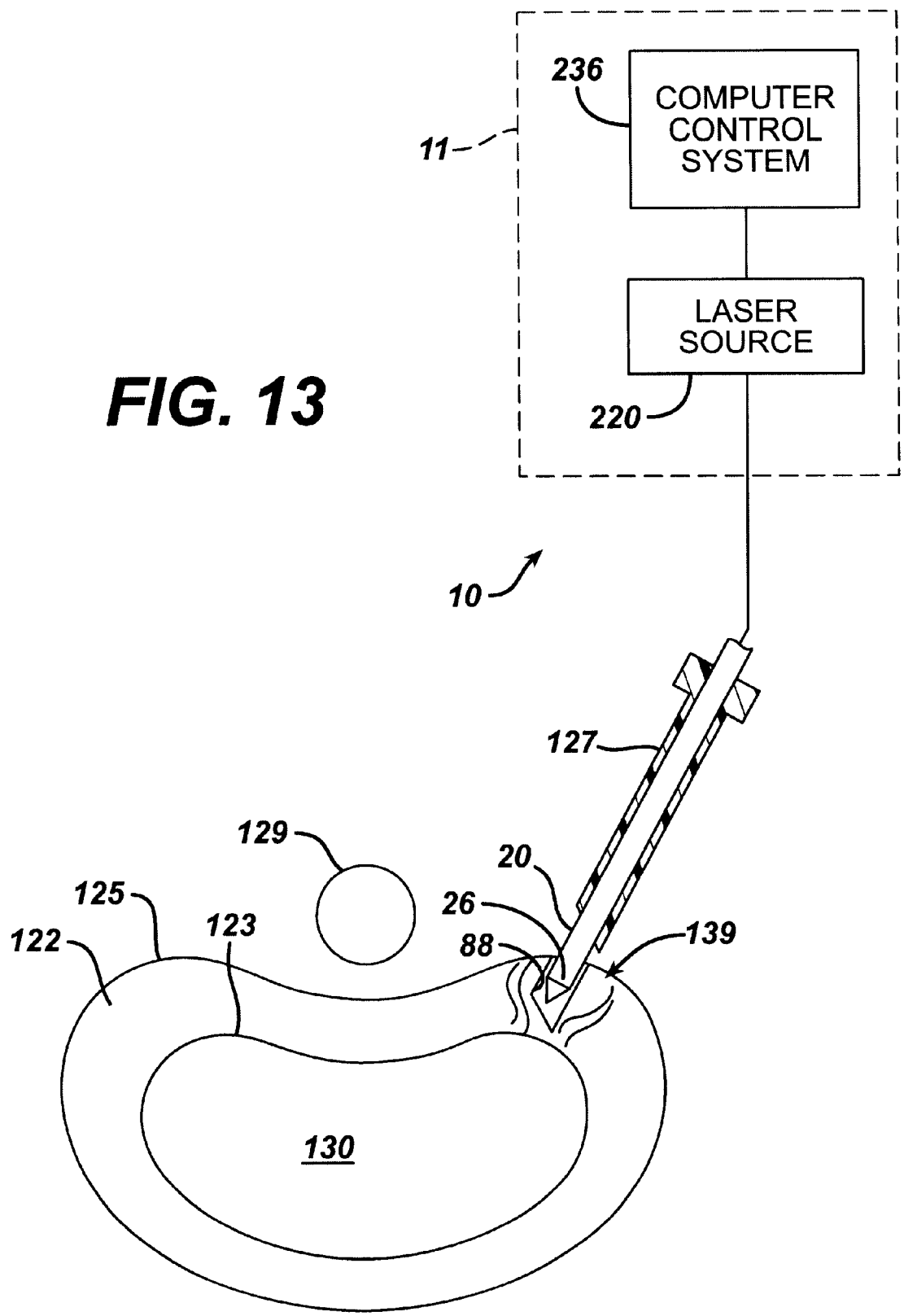
FIG. 13 is a schematic view showing a method of introducing a diffuser into the annulus of an intervertebral disc.

Referring now to FIG. 13, a method for heating the annulus of an intervertebral disc while avoiding inserting the device into the nucleus is shown schematically. Optical fiber 20 may be about 65 centimeters long and about one to two millimeters in diameter. Optical fiber 20 can incorporate thermometry using a temperature measurement device containing a light reactive material, such as, for example, alexandrite, to fluoresce in a temperature dependent manner.

A channel 88 is formed in annulus 122 by inserting sharp-ended tubular needle 127, as shown in FIG. 13. A light source that emits diffuse light, such as optical fiber 20 comprising diffuser 26, is connected to laser 11 (shown schematically) to create a laser treatment system 10. Optical fiber 20 of laser treatment system 10 is inserted into annulus 122 of intervertebral disc near damage zone 139 to a position where diffuser 26 is within an inner wall 123 and an outer wall 125 of annulus 122 inside channel 88. Optical fiber 20 may be placed by pushing optical fiber 20 through the bore of sharp-ended tubular needle 127. Optical fiber 20 may be placed utilizing, for example, ultrasonic guidance or magnetic resonance imaging guidance to obtain an image of optical fiber 20 and surrounding tissue. Laser 11 delivers diffuse light energy through optical fiber 20 to heat the portion of annulus 122 in contact or near diffuser 26. Application of a phototheramic dosage will produce the desired temperature in the damaged zone 139 of annulus 122 without damaging spinal cord 129 or nucleus 130. The damaged zone 139 may be heated to a temperature level to cause a change in physical characteristics of annulus 122 within damaged zone 139. The damaged zone 139 may be, for example, heated to a temperature to cause damage to pain-causing nerve endings that have grown into annulus 122 in the region of damaged zone 139. The damaged zone 139 may also be, for example, heated to a temperature to cause collagen of annulus 122 within damaged zone 139 to shrink without ablating or vaporizing nucleus 130. It has been found that ingrown annulus nerve endings become damaged at a temperature at about 45° C., while collagen shrinks at about a temperature of 60° C. Nucleus 130 would vaporize at a temperature of approximately 80° C. to a temperature of approximately 100° C.

The patient can realize advantages of inserting diffuser 26 into annulus 122 to directly heat annulus 122 without inserting devices through nucleus 130. By utilizing the method of heating annulus 122 with diffuser 26 inside annulus 122, heating can be confined to the region of damaged zone 139 of annulus 122. Furthermore, the method of inserting diffuser 26 directly into annulus 122 creates channel 88 within damaged zone 139, eliminating the necessity of creating a channel 88 in a healthy portion of annulus 122. By transferring heat directly to annulus 122 with diffuser 26 inside the annulus, the annulus can be heated to a temperature higher than nucleus 118. Heating annulus 122 directly allows annulus 122 to be raised to a therapeutic temperature without the necessity of raising the nucleus temperature to a value higher than the therapeutic temperature needed in annulus 122. As a further treatment, a physician can continue to cause diffuser 26 to emit light as optical fiber 20 is withdrawn from channel 88. Continuing to emit diffuse light from diffuser 26 can raise the temperature of annulus 122 near channel 88 to heat channel 88 to cause shrinkage of collagen of annulus 122 in the vicinity of channel 88 as optical fiber 20 is withdrawn.

Optical temperature measurements of the tissue in the vicinity optical fiber 20 can be made. When diffuser 26 touches annulus 122, optical temperature measurements of annulus 122 can be made by, for example, utilizing computer controlled methods and temperature dependant fluorescing materials described herein. Optical temperature measurements can then be communicated to laser 11. Computer control can then be used to vary the output light intensity from optical fiber 20 based on the temperature measurements of annulus 122.

Figure 14:
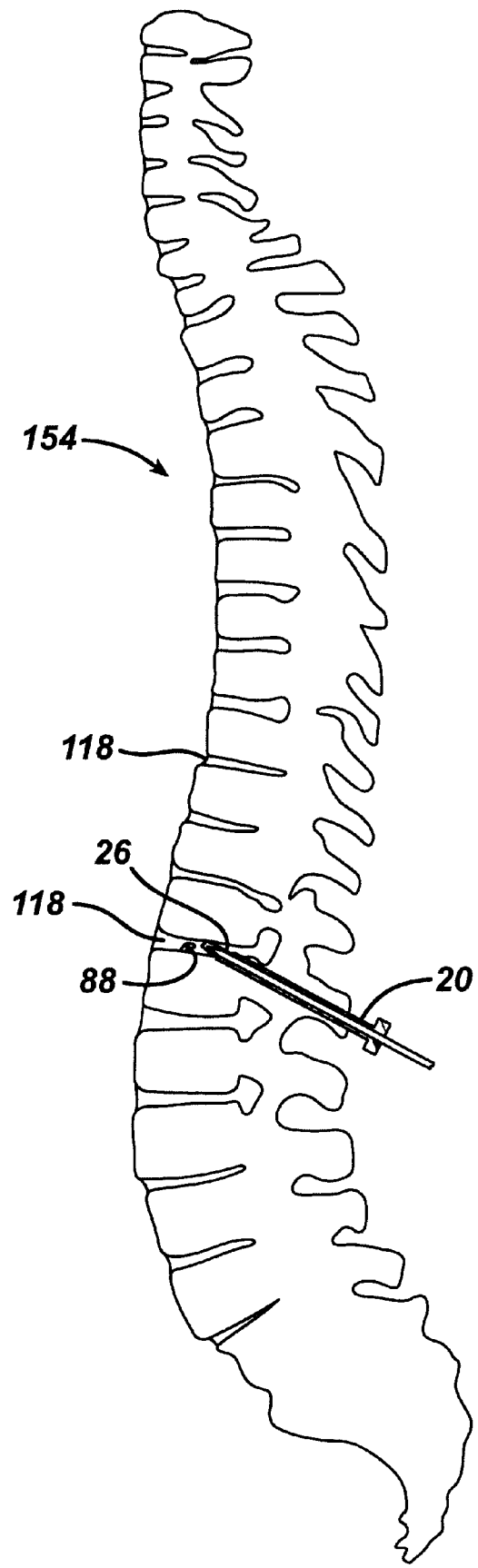
FIG. 14 is a schematic representation of the spine showing a diffuser inserted a second time into an annulus of an intervertebral disc, and also representing other annuli into which a diffuse light source could be inserted.

FIG. 14 demonstrates schematically that diffusers 26 can be placed, as desired, into other annuli 122 through channels 88 in spine 154 and light energy can be applied interstitially as taught above. A diffuser 26 on optical fiber 20 is placed into a second intervertebral disc 118 and aligned within annulus 122 of the second intervertebral disc 118. Diffuse light is then used to heat annulus 122 of the second intervertebral disc 118 in the same manner as taught above. The diffuse light will radiantly heat the annulus 122 of the second intervertebral disc 118 to the desired temperature to destroy nerve endings or to cause shrinkage of the collagen contained within the annulus 122 of the second intervertebral disc 118.

Optical fibers 20 may also be placed, if desired, into another portion of the same annulus 122 to heat the other portion of annulus 122. Diffuser 26 of optical fiber 20 is placed into a second portion of annulus 122 and diffuse light is applied in a controlled manner in the method taught above. The diffuse light will radiantly heat the second portion of annulus 122 to the desired temperature to destroy nerve endings or to cause shrinkage of the collagen contained within the second portion of the annulus 122 of the same intervertebral disc 118.

As with the first application of heat to annulus 122, computer control can be employed to control and to monitor annulus temperature when applying heat to either the same annulus 122 for a second time or to another annulus 122 for the first time.

Figure 15:
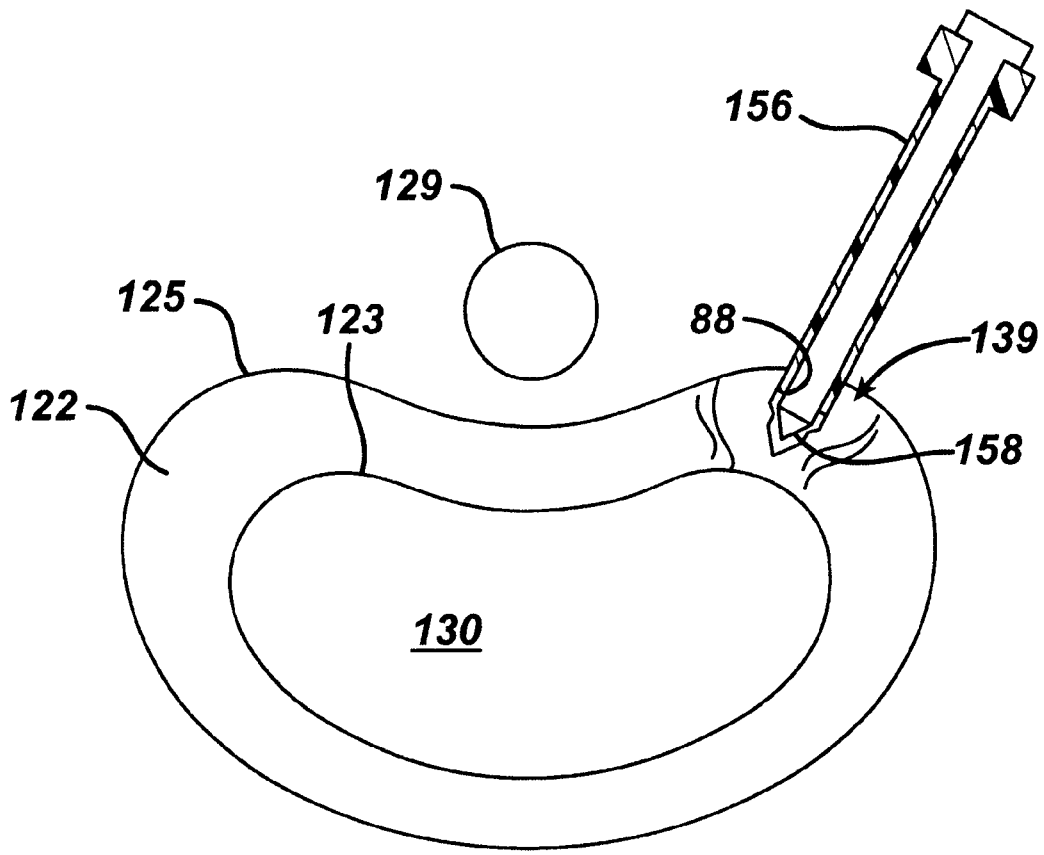
FIG. 15 is a schematic view showing a method of introducing a piercing needle with a blunt-ended cannula into the annulus of an intervertebral disc.

It will be recognized that equivalent structures may be substituted for the structures illustrated and described herein and that the described embodiment of the invention is not the only structure which may be employed to implement the claimed invention. For example, FIG. 15 shows blunt-ended cannula 156 containing a piercing needle in the bore and extending from the distal end could substitute for sharp-ended tubular needle 127. A physician can alternatively insert piercing needle 158 through the inner diameter of blunt-ended cannula 156 and use the assembly to pierce annulus 122. After piercing channel 88 into annulus 122, a physician can remove the piercing needle 158 and have available an open blunt-ended cannula for insertion of optical fiber 20. Optical fiber 20, or any light source, may be inserted through blunt-ended cannula 156. The physician can then supply power to the light source to emit diffuse light to heat annulus 122 of intervertebral disc 118 to a therapeutic temperature as described above. The physician can also use piercing needle 158 and blunt-ended cannula 156 in the same manner described above to pierce the same annulus 122 a second time to heat another portion of annulus 122, or to pierce a second annulus 122 of a second intervertebral disc 118.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method of controllably heating an annulus of an intervertebral disc while avoiding a nucleus of said intervertebral disc, wherein said method comprises the steps of:
    providing a diffuser for emitting light energy;
    forming an access channel into said annulus of said intervertebral disc while avoiding said nucleus of said intervertebral disc;
    inserting said diffuser into said access channel created within said annulus; and
    activating said diffuser to emit diffuse light having an intensity sufficient to heat at least a first portion of said annulus to a predetermined temperature while said diffuser remains within said access channel within said annulus, wherein said predetermined temperature is sufficient to cause a change in at least one characteristic of tissue in said annulus.

2. A method according to claim 1 wherein said first portion comprises a damaged zone of said annulus, and said damaged zone of said annulus is heated to said predetermined temperature while a second portion of said annulus remains at a temperature below said predetermined temperature.

3. A method according to claim 2 wherein said predetermined temperature is sufficient to destroy nerve endings within said first portion of said annulus.

4. A method according to claim 2 wherein said annulus comprises collagen, and wherein said predetermined temperature is sufficient to cause shrinkage of said collagen.

5. A method according to claim 4 wherein said intervertebral disc further comprises a nucleus, and further comprises the step of maintaining said nucleus at a second temperature below which vaporization of said nucleus occurs.

6. A method according to claim 1 wherein said step of providing a diffuser comprises providing an optical fiber having a diffuser, said optical fiber having a continuous, unitary outer sleeve extending from a distal end of said optical fiber to a connector of said optical fiber.

7. A method according to claim 1 further comprising inserting a sharp-ended, hollow needle into said annulus to form said access channel.

8. A method according to claim 7 wherein said diffuser is inserted through said sharp-ended, hollow needle.

9. The method according to claim 1 further comprising the steps of:
    removing said diffuser from said access channel;
    forming a second access channel through said annulus of said intervertebral disc while avoiding said nucleus of said intervertebral disc;
    inserting said diffuser a second time into said second access channel created within said annulus; and
    activating said diffuser a second time to emit diffuse light having an intensity sufficient to heat at least a second portion of said annulus to a predetermined temperature while said diffuser remains within said second access channel within said annulus, wherein said predetermined temperature is sufficient to cause a change in at least one characteristic of tissue in said annulus.

10. A method according to claim 9 wherein said second portion of said annulus is heated to said predetermined temperature while a third portion of said annulus remains at a temperature below that which is sufficient to cause a change in the characteristics of said annulus.

11. A method according to claim 10 wherein said predetermined temperature is sufficient to destroy nerve endings within said annulus in said second portion of said annulus.

12. A method according to claim 10 wherein said annulus comprises collagen, and wherein said predetermined temperature is sufficient to cause shrinkage of said collagen.

13. A method according to claim 12 wherein said intervertebral disc comprises a nucleus, and said nucleus is maintained below a second temperature at which vaporization of said nucleus occurs.

14. A method of controllably heating an annulus of an intervertebral disc while avoiding a nucleus of said intervertebral disc, wherein said method comprises the steps of:
providing a diffuser for emitting light energy;
providing an optical temperature measuring component;
forming an access channel into said annulus of said intervertebral disc while avoiding said nucleus of said intervertebral disc;
inserting said diffuser into said access channel created within said annulus;
optically measuring a temperature of tissue in said annulus; and
activating said diffuser to emit diffuse light having an intensity sufficient to heat at least a first portion of said annulus to a predetermined temperature while said diffuser remains within said access channel within said annulus, wherein said predetermined temperature is sufficient to cause a change in at least one characteristic of tissue in said annulus.

15. The method according to claim 14 wherein said temperature measuring component comprises a fluorescent material, and said fluorescent material emits a second light having an intensity that decays in a temperature dependent manner when said temperature measuring component is illuminated with a first light in a predetermined wavelength.

16. The method of claim 15 wherein said optically measuring said temperature comprises the steps of:
emitting said first light at said predetermined wavelength utilizing a light generator, said first light at said predetermined wavelength having a first intensity that varies periodically as a function of time;
sensing said second light, said second light having a second intensity that varies periodically as a function of time; and
comparing said periodically varying first intensity of said first light and said periodically varying second intensity of said second light to determine a phase angle to determine said temperature.

17. The method of claim 16 wherein said fluorescent material comprises alexandrite.

18. A method of controllably heating an annulus of an intervertebral disc while avoiding a nucleus of said intervertebral disc, wherein said method comprises the steps of:
providing a diffuser for emitting light energy;
inserting a needle into an inner diameter of a cannula to cause said needle to extend beyond a distal end of said cannula;
forming an access channel through said annulus of said intervertebral disc using said needle and said cannula while avoiding said nucleus of said intervertebral disc;
removing said needle from said cannula to create an opening through said cannula to insert said diffuser;
inserting said diffuser through said cannula into said access channel created within said annulus; and
activating said diffuser to emit diffuse light having an intensity sufficient to heat at least a first portion of said annulus to a predetermined temperature while said diffuser remains within said access channel within said annulus, wherein said predetermined temperature is sufficient to cause a change in at least one characteristic of tissue in said annulus.

* * * * *